(12) United States Patent
Stein (10) Patent No.: US 8,829,432 B2
(45) Date of Patent: Sep. 9, 2014

(54) SYSTEM AND METHODS FOR DETERMINING MOLECULES USING MASS SPECTROMETRY AND RELATED TECHNIQUES

(71) Applicant: Brown University, Providence, RI (US)

(72) Inventor: Derek M. Stein, Boston, MA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 13/848,142

(22) Filed: Mar. 21, 2013

(65) Prior Publication Data

US 2013/0233700 A1  Sep. 12, 2013

Related U.S. Application Data

(63) Continuation of application No. 13/056,755, filed as application No. PCT/US2009/004400 on Jul. 30, 2009, now Pat. No. 8,426,807.

(60) Provisional application No. 61/085,480, filed on Aug. 1, 2008.

(51) Int. Cl.

| | |
|---|---|
| *B01J 19/00* | (2006.01) |
| *C12Q 1/00* | (2006.01) |
| *H01J 49/04* | (2006.01) |
| *B01J 19/12* | (2006.01) |
| *B01D 67/00* | (2006.01) |
| *B01J 19/08* | (2006.01) |
| *C12Q 1/68* | (2006.01) |

(52) U.S. Cl.
CPC ........... *B01J 19/087* (2013.01); *H01J 49/0409* (2013.01); *B01J 19/121* (2013.01); *B01D 67/006* (2013.01); *C12Q 1/6872* (2013.01); *C12Q 1/6869* (2013.01)

USPC ........... 250/290; 250/281; 250/282; 250/284; 250/288; 250/291

(58) Field of Classification Search
USPC .................. 250/281, 282, 284, 288, 290, 291
See application file for complete search history.

(56) References Cited

U.S. PATENT DOCUMENTS 5,608,216 A * 3/1997 Wells et al. .................... 250/282
5,770,857 A * 6/1998 Fuerstenau et al. ........... 250/281
(Continued)

OTHER PUBLICATIONS

"Q&A: Derek Stein on Marrying Nanopores and Mass Spec for Single-Molecule Sequencing," Genome Web Article dated May 26, 2009 (web page).

(Continued)

*Primary Examiner* — David A Vanore
(74) *Attorney, Agent, or Firm* — Wolf, Greenfield & Sacks, P.C.

(57) ABSTRACT

The present invention generally relates to mass spectrometry and related techniques, and in some cases, to determining single species using mass spectrometry. In certain instances, polymers such as DNA or RNA can also be sequenced. Certain embodiments of the invention relate to passing a polymer, such as DNA, RNA, a protein, a polypeptide, a polysaccharide, etc., through a pore and cleaving the polymer in sequence. For instance, the polymer may be cleaved using a laser or an electric field. In some embodiments, a property of at least one subunit of a polymer is determined using mass spectrometry. In some embodiments, a single ion (which may be a subunit of a polymer, or an ion based on another species) can be isolated in a mass spectrometer and a signal generated from the single ion.

28 Claims, 5 Drawing Sheets

(56) References Cited

U.S. PATENT DOCUMENTS

| | | | |
|---|---|---|---|
| 6,238,871 | B1 | 5/2001 | Koster |
| 6,322,970 | B1 | 11/2001 | Little et al. |
| 6,392,226 | B1 * | 5/2002 | Takada et al. ............... 250/292 |
| 6,762,406 | B2 * | 7/2004 | Cooks et al. ............... 250/292 |
| 7,122,791 | B2 * | 10/2006 | Joyce et al. ............... 250/288 |
| 7,157,698 | B2 * | 1/2007 | Makarov et al. ............. 250/281 |
| 7,276,266 | B1 * | 10/2007 | Khare et al. ............... 427/533 |
| 7,342,224 | B2 * | 3/2008 | Makarov et al. ............. 250/290 |
| 7,473,436 | B1 * | 1/2009 | Khare et al. ............. 427/248.1 |
| 7,507,953 | B2 * | 3/2009 | Makarov et al. ............. 250/287 |
| 7,767,270 | B1 * | 8/2010 | Khare et al. ............... 427/535 |
| 7,825,374 | B2 * | 11/2010 | Cotter et al. ............... 250/287 |
| 7,902,345 | B2 * | 3/2011 | Van Den Boom et al. ... 536/23.1 |
| 8,038,887 | B2 * | 10/2011 | Bakajin et al. ............... 210/652 |
| 8,143,009 | B2 * | 3/2012 | Snodgrass ............... 435/6.13 |
| 8,426,807 | B2 * | 4/2013 | Stein ............................ 250/282 |
| 2004/0149580 | A1 | 8/2004 | Flory |
| 2004/0262512 | A1 | 12/2004 | Tobita et al. |
| 2005/0186576 | A1 | 8/2005 | Chan et al. |
| 2006/0063171 | A1 | 3/2006 | Akeson et al. |
| 2006/0073489 | A1 * | 4/2006 | Li et al. ........................... 435/6 |
| 2006/0234252 | A1 | 10/2006 | Andersen |
| 2008/0223795 | A1 * | 9/2008 | Bakajin et al. ............... 210/767 |
| 2010/0092952 | A1 * | 4/2010 | Ju et al. ........................... 435/6 |
| 2011/0160093 | A1 * | 6/2011 | Van Den Boom et al. ...... 506/16 |
| 2011/0172115 | A1 * | 7/2011 | Thompson ....................... 506/9 |
| 2011/0204219 | A1 * | 8/2011 | Stein ............................ 250/282 |
| 2012/0091005 | A1 * | 4/2012 | Burrows et al. ............... 204/605 |
| 2012/0142904 | A1 * | 6/2012 | He et al. ....................... 530/412 |
| 2012/0152742 | A1 * | 6/2012 | Gorfinkel et al. ............. 204/452 |
| 2012/0172258 | A1 * | 7/2012 | Eshoo et al. ................... 506/26 |

OTHER PUBLICATIONS

International Search Report and Written Opinion for International Application No. PCT/US09/04400 mailed Nov. 12, 2009.

Office Action from U.S. Appl. No. 13/056,755, date of mailing Sep. 17, 2012.

Robertson et al., "Single-Molecule Mass Spectrometry in Solution Using a Solitary Nanopore," PNAS, 2007 May 15, vol. 104, No. 20, pp. 8207-8211.

Stein et al., "Nanopore Mass Spectrometry," Abstract submitted for the Mar. 2012 Meeting of the American Physical Society, Feb. 22, 2012, XP55020133, retrieved from http://absimage.aps.org/image/MWS_Mar12-2011-007338.pdf, Abstract Only.

Supplementary European Search Report for EP 09 80 3271.7, date of mailing Mar. 8, 2012.

European Office Action from Application No. 09 803 271.7, date of mailing Oct. 4, 2013.

Robertson et al., "Single molecule mass spectrometry in solution using a solitary nanopore," PNAS, May 15, 2007, vol. 104, No. 20, pp. 8207-8211.

Rodrigues et al., "Evolution of charged species in propane/air flames: mass-spectrometric analysis and modelling," Plasma Sources Sci. Technol., 2007, vol. 16, No. 1, pp. 161-172 (published Dec. 20, 2006).

* cited by examiner

SYSTEM AND METHODS FOR DETERMINING MOLECULES USING MASS SPECTROMETRY AND RELATED TECHNIQUES

RELATED APPLICATIONS

This application is a continuation of U.S. patent application Ser. No. 13/056,755, having a §371(c) date of May 2, 2011, entitled "System and Methods for Determining Molecules Using Mass Spectrometry and Related Techniques," which is a national stage filing under 35 U.S.C. §371 of PCT Apl. No. PCT/US2009/004400, filed Jul. 30, 2009, entitled "System and Methods for Determining Molecules Using Mass Spectrometry and Related Techniques," which claims the benefit of U.S. Pat. Apl. Ser. No. 61/085,480, filed Aug. 1, 2008, entitled "System and Methods for Determining Molecules using Mass Spectrometry and Related Techniques," each incorporated herein by reference.

FIELD OF THE INVENTION

The present invention generally relates to mass spectrometry and related techniques, and in some cases, to determining single species using mass spectrometry. In certain instances, polymers such as DNA or RNA can also be sequenced.

BACKGROUND OF THE INVENTION

Deoxyribonucleic acids (DNA), ribonucleic acids (RNA), and proteins comprise linear polymers which often have particular sequences of monomer units. High speed and low cost methods for determining the sequence of each of these types of molecules are desired, for example, to assist basic biological studies and the development of health case applications, among other goals. The demand for sequencing is perhaps highest with DNA, and conventional DNA sequencing methods often require multiple copies of the target sequence and chemical synthesis reactions. The sequencing speed depends on factors such as the rate of such chemical reactions, or the cost of the necessary chemical reagents and the labor and energy needed to carry out the reactions.

SUMMARY OF THE INVENTION

The present invention generally relates to mass spectrometry and related techniques, and in some cases, to determining single species using mass spectrometry. In certain instances, polymers such as DNA or RNA can also be sequenced. The subject matter of the present invention involves, in some cases, interrelated products, alternative solutions to a particular problem, and/or a plurality of different uses of one or more systems and/or articles.

In one aspect, the invention is directed to a method. According to a first set of embodiments, the method includes acts of passing an polynucleotide through a non-naturally occurring pore having a diameter of less than about 1 micrometer, and cleaving the polynucleotide in sequence. In another set of embodiments, the method includes acts of passing an polynucleotide through a non-naturally occurring pore having a diameter of less than about 1 micrometer, and cleaving the polynucleotide using a laser or an electric field.

The method, in accordance with yet another set of embodiments, includes acts of isolating a single ion in a mass spectrometer, generating a signal in the mass spectrometer using the single ion, and obtaining a mass spectrograph based on the signal, indicative of the single ion. In still another set of embodiments, the method includes acts of passing a polymer through a pore having a diameter of less than about 1 micrometer, and determining a property of at least one subunit of the polymer using mass spectrometry.

In one set of embodiments, the method includes acts of passing a polymer through a pore having a diameter of less than about 1 micrometer, sequentially cleaving the polymer as it passes through the pore to produce a plurality of fragments, and ionizing one or more of the fragments. In another set of embodiments, the method includes acts of passing a single molecule through a pore having a diameter of less than about 1 micrometer, creating at least one ion from the single molecule, and determining a property of the at least one ion.

The invention is directed to a system, in another aspect. According to one set of embodiments, the system includes a pore having a diameter of less than about 1 micrometer, separating a low-pressure chamber and a sample chamber, a particle source configured to direct particles in the low-pressure chamber towards the pore, and a mass detection unit configured to determine ions produced within the low-pressure chamber.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to mass spectrometry and related techniques, and in some cases, to determining single species using mass spectrometry. In certain instances, polymers such as DNA or RNA can also be sequenced. Certain embodiments of the invention relate to passing a polymer, such as DNA, RNA, a protein, a polypeptide, a polysaccharide, etc., through a pore and cleaving the polymer in sequence. For instance, the polymer may be cleaved using a laser or an electric field. In some embodiments, a property of at least one subunit of a polymer is determined using mass spectrometry. In some embodiments, a single ion (which may be a subunit of a polymer, or an ion based on another species) can be isolated in a mass spectrometer and a signal generated from the single ion.

One aspect of the present invention is generally directed to systems and methods of sequencing a polymer using mass spectrometry and related techniques. In some instances where the species is a polymer, the polymer may be any polymer, including biopolymers or other organic polymers. Non-limiting examples of biopolymers include a polynucleotide (e.g. DNA, RNA, etc.), a polypeptide (e.g. a protein, a hormone, etc.), a polysaccharide, (e.g. heparin, hyaluronic acid, glycogen, cellulose, chitin, etc.), or the like, as well as combinations of these. The biopolymer may be, for example, a naturally occurring molecule and/or may be derived from a biological source, such as a cell, or the biopolymer may be produced synthetically, for example on an automated synthesis machine. A biopolymer may also be a non-naturally occurring composition, for example a peptide-nucleic acid or a locked nucleic acid. The biopolymer may include other non-biopolymeric entities in some cases, for example fluorophores or other indicators, other polymers such as poly(ethylene glycol), etc.

Figure 5:
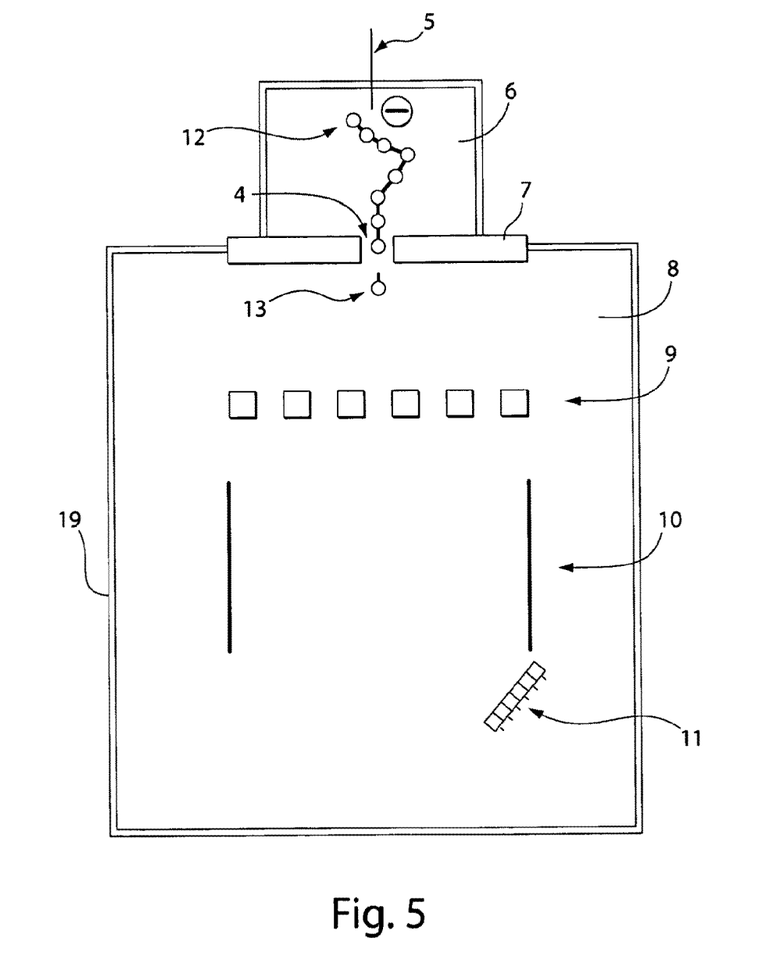
FIG. 5 illustrates a mass spectrometer device in another embodiment of the invention.

In one set of embodiments, a species, such as a biopolymer, is passed through a pore, and the species is determined via mass spectrometry. FIG. 5 illustrates an example of one embodiment of the invention, and shows polymer 12, such as DNA, in chamber 6. (Polymer 12 is used in this example as an illustrative embodiment; in other cases, however, other species may be used as well, as discussed below.) Polymer 12 passes or "translocates" through pore 4 in membrane 7, emerges in chamber 8, which may be operated at reduced pressure in some cases. In some cases, an electric field generated by electrodes 5 and 9 can be used to urge the polymer through pore 4. Other techniques besides electric fields can also be used to urge the polymer through the pore, as discussed below. In addition, in some cases, the pore may be of a size comparable to the width of the polymer (or other species) passing through the pore. As the polymer emerges from the pore, monomers 13 are dissociated from polymer 12. The monomers may be dissociated, for example, by an ionic beam, by an electric field, or the like, as discussed below. Monomer 12 can be accelerated through mass spectrometer 19 using a magnetic field created by magnetic region 10, before impinging on a detector 11, from which an output can be recorded.

Virtually any suitable species can be analyzed or determined in such a system. The species may be a molecule or atom, or a plurality of molecules or atoms, some or all of which may be charged or uncharged, etc. For example, the species may be an organic molecule, an inorganic molecule, a polymer (such as described above), etc. Accordingly, the invention is not necessarily limited to only the determination of polymers. As used herein, the term "determining" generally refers to the analysis of a species and/or signal, for example, quantitatively or qualitatively, and/or the detection of the presence or absence of the species or signals. For example, an ion may be determined by analyzing the mass/charge ratio of the ion or otherwise obtaining a quantity from which the molecular weight of the ion can be derived.

As mentioned, the species is passed through a pore in one set of embodiments. A pores is generally a hole or an opening with a dimension of less than about 1 micron in a membrane or other surface. In some cases, the membrane is continuous and solid, i.e., having only one pore present, although in some embodiments of the invention, more than one pore may be present in a membrane. In some cases, the pore may have a dimension less than about 500 nm, less than about 250 nm, or less than about 100 nm. In other cases, the pore may have a dimension less than about 50 nm, less than about 30 nm, less than about 15 nm, less than about 10 nm, less than about 5 nm, or less than about 2 nm. In some embodiments, the pore may have a dimension between about 1 nm and about 5 nm, between about 4 nm and about 30 nm, between about 25 nm and about 100 nm, etc. In some cases, the pore may have a dimension between about 50 nm and about 250 nm, between about 200 nm and about 500 nm, between about 400 nm and about 700 nm, between about 500 nm and about 1000 nm, etc. The actual size of the pore will vary, depending on the particular application, but will often be of dimensions comparable to dimensions of the species to be passed through the pore. Those of ordinary skill in the art will be able to determine the dimension of pore through routine experimentation using a variety of known techniques. In one embodiment, for instance, electron microscopy can be used to determine the size of the pore.

The pore may be of any shape and dimension. For instance, the pore can be generally circular, octagonal, hexagonal, pentagonal, rectangular, or triangular, etc. In some cases, the pore may have an irregular shape. The vertices of such structures may be vaguely defined, i.e. rounded, or sharp, or a combination of rounded and sharp. The sides or edges of the pore, on the surface or within the membrane comprising the pore may be similar in length, for example in the case of a square, or may be different, such as in a rectangle or non-ordered shape. In one embodiment, the pore may have a general slit-like structure. The shape or dimensions of the pore on one side of the membrane may be the same or different from the shape or dimensions of the pore on the other side of the membrane. In one set of embodiments, the pore is non-naturally created. For instance, a pore may be created by creating a hole in a membrane, for example, using a laser.

In some aspects of the invention, a plurality of pores may be present in the membrane. In some instances, each pore of the plurality or pores may be similarly sized, and in other instances, the plurality of pores may contain a range of pore sizes. As mentioned, the pore may be formed in a membrane. The membrane may be constructed out of any suitable material. Typically, the membrane is formed from materials suitable for preventing passage of species therethrough, except for passage through the pore. For instance, the membrane may be constructed of solid state and/or polymeric and/or ceramic materials, e.g. inorganic and organic materials, oxides, films, etc. Such materials are known to those skilled in the art. Specific, non-limiting examples include silicon, germanium, and compounds comprising silicon, such as silicon carbide and silicon nitride. The materials used may be a conductor in some cases, such as gold, palladium, platinum, copper, nickel, aluminum, iron, silver, etc. Polymeric materials may also be used, such as photoresists and plastics, e.g. PMMA, epoxies, polyethylene, polypropylene, etc. In other instances, conducting polymers exemplified by polythiophene and polypyrrole can be used. In certain embodiments, one side of the membrane comprises silicon nitride and the other side comprises a metalized surface. In one embodiment, the silicon nitride side of the membrane is exposed to aqueous solution and the metalized side is exposed to an atmosphere of lower pressure, i.e. a vacuum.

In some instances, a carbon nanotube may be used to form a pore. A carbon nanotube pore may be formed, for example, by embedding the carbon nanotube within a material (e.g., glass, silica, or other materials such as those described herein) and sectioning the material such that a membrane is formed containing a carbon nanotube pore. In some instances, ions or molecules may be passed through the interior of the carbon nanotube. The carbon nanotube may have any suitable diameter, e.g., having an average diameter of less than about 500 nm, less than about 250 nm, or less than about 100 nm. In other cases, the pore may have a dimension less than about 50 nm, less than about 30 nm, less than about 15 nm, less than about 10 nm, less than about 5 nm, or less than about 2 nm. In some embodiments, the pore may have a dimension between about 1 nm and about 5 nm, between about 4 nm and about 30 nm, between about 25 nm and about 100 nm, etc. The carbon nanotube may be single-walled or multiwalled. Methods for synthesizing a carbon nanotube are known in the art.

Figure 1:
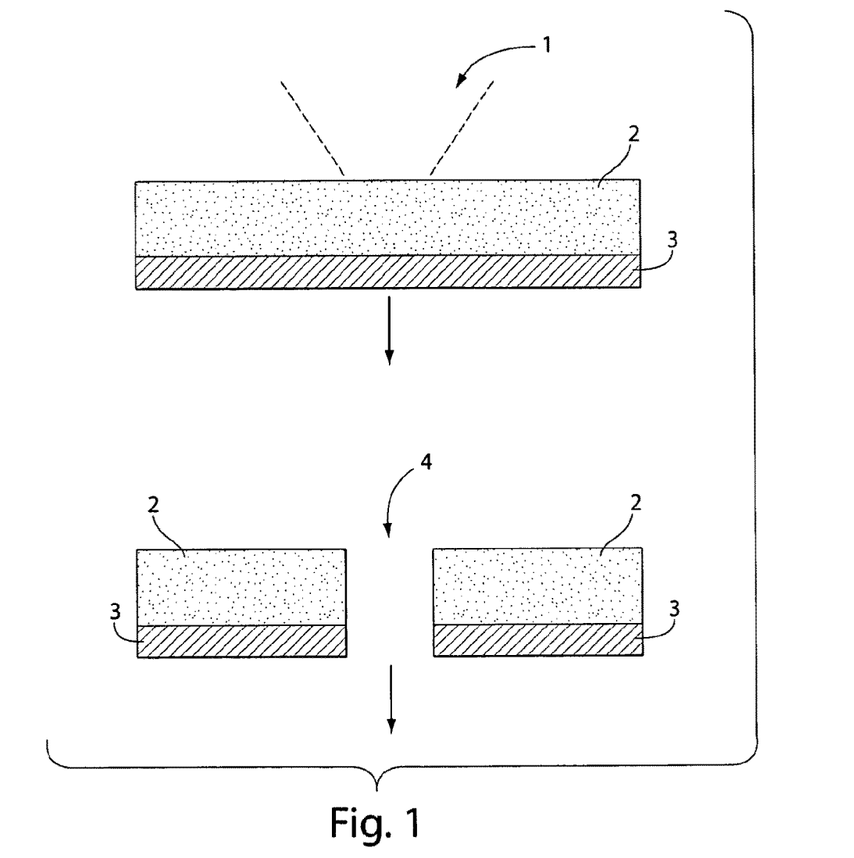
FIG. 1 shows the formation of a pore in a bilayer membrane, in accordance with various embodiments of the invention.
Figure 2:
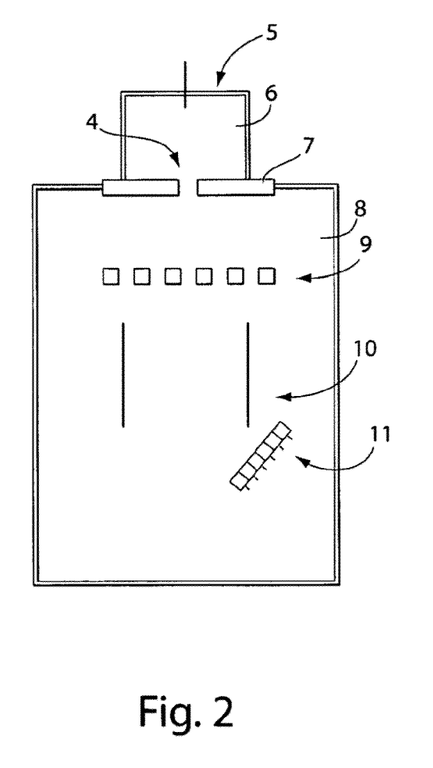
FIG. 2 shows a mass spectrometer device configured with a pore, in accordance with various embodiments of the invention.

In one embodiment, the pore may be a hole in an otherwise continuous thin membrane made of a solid material. A membrane, as can be seen in the example of FIG. 1, may comprise a layer of a solid-state insulator such a silicon nitride or silicon dioxide 1 and a layer of a metal conductor such as gold or platinum 2. A variety of techniques are known in the art for fabricating pores such as ion beam sculpting and electron-beam lithography followed by etching. FIG. 1 illustrates one method using a transmission electron beam 1 to obliterate a membrane comprising an insulator 2 and a conductor 3 to form a pore 4. The thickness of each material layer comprising the membrane may be between 5 nm and 100 nm. In some instances a layer may be less than about 2 nm, less than about 5 nm, less than about 10 nm, less than about 20 nm, less than about 30 nm, less than about 50 nm, less than about 75 nm, less than about 100 nm, less than about 150 nm, less than about 200 nm, etc. In other instances, the thickness of the layer may be between about 2 nm to 10 nm, between about 5 nm to 20 nm, between about 10 nm to 30 nm, between about 20 nm to 50 nm, between about 30 nm to 75 nm, between about 50 nm to 100 nm, between about 75 nm to 150 nm, between about 100 nm to 200 nm, etc. In some embodiments, the layer may be greater than 200 nm thick. The conductor layer constitutes an electrode, the potential of which is controlled. The conducting side of the membrane may be sealed within a vacuum chamber that can house a mass spectrometer as can be seen in FIG. 2.

In some aspects, the pore separates a sample chamber 6 from a reduced pressure chamber 8, i.e. a vacuum chamber. The pressure change between the two chambers may be, for example a change of 25%, 50%, or 75% of the lower pressure chamber, relative to the higher pressure chamber. In some cases, the pressure change may be of several orders of magnitude. For instance, the higher pressure chamber may be approximately at atmospheric pressure while the lower pressure chamber may have a pressure of less about than 1 mmHg, less than about 0.1 mmHg, or less than about 0.01 mmHg Such changes in pressure can be created, for example, using suitable pressure or vacuum pumps in fluidic communication with either side of the membrane defining the pore.

In some embodiments, the sample chamber 6 contains an aqueous solution in which candidate molecules are dissolved. The temperature and pressure of the chamber may controlled. The solution can contain a variety of additives including salts, buffers, and chaotropic agents such as guanidine hydrochloride, urea, or organic solvents. In certain embodiments, the temperature, chemical composition, and/or pH of the sample chamber solution can be adjusted to create conditions conducive to denaturation of molecules, for example of proteins and nucleic acids. In some embodiments, a reduced pressure chamber 8 exists on the side of the membrane and pore opposite of the sample chamber 6. It is to be understood that the term "vacuum" as used herein does not necessarily imply a perfect vacuum and in most instances refers to a region of lower pressure relative to another region. In some embodiments the vacuum is a pressure of less than about 760 mmHg, less than about 500 mmHg, less than about 100 mmHg, less than about 10 mmHg, less than about 1 mmHg, less than about 0.1 mmHg, less than about 0.001 mmHg, less than about 50 microns of Hg, less than about 10 microns of Hg, less than about 1 micron of Hg, or less than about 0.001 microns of Hg. It is understood that 760 mmHg is equivalent to 101325 Pa.

Figure 3:
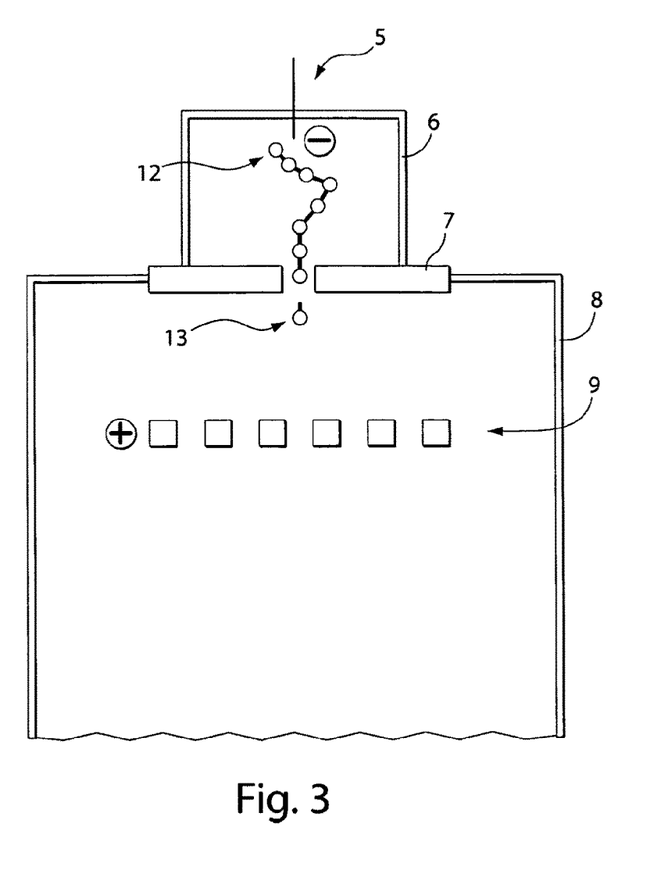
FIG. 3 shows the translocation of a polymer through a pore and the ionization and dissociation of a fragment of the polymer, in accordance with various embodiments of the invention.

In another aspect of the invention, the pore or device comprising the pore is configured to allow molecules to traverse the pore as seen in FIG. 3. In some embodiments, the traversal of molecules occurs one at a time and in single file fashion. "Single file" is defined as each monomer moving through a pore one at a time and in sequence. A polymer passing through a pore in single file fashion typically will not fold upon itself within the pore. A molecule can be made to traverse a pore, i.e. pass from one side of the pore to the other side of the pore by traveling within the pore, using a variety of methods known to those skilled in the art.

In one embodiment, an electrical potential can be used to urge charged species, such as proteins and nucleic acids, through the pore. The magnitude of the potential, regardless of sign, may be greater than about 0.001 V, greater than about 0.01 V, greater than about 0.1 V, greater than about 1 V, greater than about 10 V, greater than about 100 V, greater than about 1000 V, or greater than about 10000 V. In other embodiments, the potential may be between about 0 V and 0.01V, about 0.001 V and 0.1 V, about 0.01 V and 1 V, about 0.1 V and 10 V, about 1 V and 100 V, about 10 V and 1000 V, or about 100 V and 10000 V. It should be understood that the actual voltage used will depend on the specific application, and can be determined using routine experimentation. In one embodiment, the sample chamber contains an electrode 5, such as a Ag/AgCl electrode, which is inserted into the solution and in some instances can apply a negative electrochemical potential to the solution. A positive electrode 9 may be placed in the reduced pressure chamber 8 to create an electrical potential capable of translocating a negatively charged species 12, such as a nucleic acid, through the pore. In an alternative embodiment, the sample chamber 6 may contain a positive electrode and the reduced pressure chamber 8 may contain a negative electrode, thereby creating an electrical potential capable of translocating a positively charged species through the pore. I. In some instances, the voltage may be kept constant, whereas in other instances the voltage may be varied depending, for example in response to data received from another aspect of the invention, for instance, the rate or mass to charge ratio of species reaching the detector, or as part of a method for translocating particular species through the pore.

In another embodiment of the present invention, an applied pressure can be used to translocate species through the pore. For instance, an applied hydrostatic pressure difference of about 1 atm between the sample chamber and the vacuum chamber may be used to urge a species through the pore. In some embodiments, the pressure difference may be less than about 1000 atm, less than about 100 atm, less than about 10 atm, less than about 1 atm, less than about 0.1 atm, or less than about 0.01 atm. In other embodiments, the pressure difference may be between about 0 atm and 0.1 atm, about 0.01 atm and 1 atm, about 0.1 atm and 10 atm, about 1 atm and 100 atm, or about 10 atm and 1000 atm. In yet another embodiment, the pressure difference may be greater than about 1000 atm.

Certain aspects of the invention provide for an ionization source for ionizing species within or in proximity to the pore, which may be used to partially cleave a polymer (or other species) passing through the pore. An "ion" is a species that is charged in some fashion, for example, positively or negatively. In some cases, the ion may be formally neutrally charged, e.g., as in a zwitterion.

In some embodiments, an electric field is used to ionize a species. Those of ordinary skill in the art will know of methods of creating an electric field. For example, a large voltage, whose magnitude is typically several kilovolts, can be applied between a first electrode and a second electrode located at short distance away from the first electrode, typically between 1 mm and 10 cm. This applied voltage generates strong electric fields at the outlet of the pore and is used to ionize a species and accelerate it into the mass spectrometer section of the device. In some instances, the magnitude of the potential, regardless of sign, may be greater than about 100 V, greater than about 500 V, greater than about 1000 V, greater than about 2000 V, greater than about 5000 V, greater than about 10000 V, greater than about 50000 V, or greater than about 100000 V. In other instances, the potential may be between about 100 V and 500 V, about 400 V and 1000 V, about 800 V and 2000 V, about 1500 V and 5000 V, about 4000 V and 10000 V, about 8000 V and 50000 V, or about 40000 V and 100000 V. One of ordinary skill in the art would know that voltages are arbitrary and can be determined using routine experimentation.

The distance between the first electrode and the second electrode can be less than about 1 mm, less than about 5 mm, less than about 10 mm, less than about 50 mm, less than about 100 mm, less than about 500 mm, etc. In another example, the distance between the first electrode and the second electrode can be greater than about 500 mm In other instances, the distance between the first electrode and the second electrode may be between about 0.5 mm and 2 mm, about 1 mm and 5 mm, about 2 mm and 10 mm, about 5 mm and 25 mm, about 20 mm and 50 mm, about 40 mm and 100 mm, or about 90 mm and 500 mm.

In certain embodiments, the applied voltage generates strong electric fields at the outlet of the pore and is used to ionize the leading monomer 13 of a polymer 12, such as the nucleobase of a polynucleotide, and dissociate it from the trailing end of the molecule. The electric fields may also be used to accelerate the charged species 13 into a mass spectrometer configured with the pore and ionization source.

Without wishing to be bound by theory, the strong electric fields can ionize the leading moiety of a translocating polymer by the mechanism of field ionization and dissociate that moiety from the subsequent bases. In certain instances, the moiety comprises a portion of a monomeric unit. In other instances, the moiety comprises an entire monomeric unit. In some examples, the moiety comprises at least one monomeric unit and may comprise multiple monomeric units. For example, a portion comprising a portion of nucleotide may be dissociated from a polynucleotide, a portion comprising at least one nucleotide may be dissociated from a polynucleotide, a portion comprising at least one nucleotide and a portion of a second nucleotide may be dissociated from a polynucleotide, a portion comprising multiple nucleotides may be dissociated from a polynucleotide, etc. The membrane electrode ensures that the strongest electric fields are confined to the vacuum side of the device, and that the section of the polymer in the sample compartment remains intact.

In other embodiments, the ionization and/or dissociation of monomers and/or portions of monomers may be promoted by irradiation of the pore or a region near the pore with light, such as laser light. In one embodiment, the irradiation originates from the vacuum side of the device. In another embodiment, the irradiation is incident on the vacuum side of the device. In one embodiment, various monomers of a polymer can be cleaved from the rest of the polymer at the same bond. For example, each nucleotide in a polynucleotide could be cleaved from the polynucleotide at the respective sugar-phosphate bond. In another example, each nucleobase could be cleaved from a polynucleotide at the nucleobase-sugar bond. In other instances, each amino acid or part of an amino acid, such as the amino acid side group, could be cleaved from a polypeptide. Alternatively, each sugar within a polysaccharide may be cleaved from the polysaccharide. The invention disclosed herein also contemplates biopolymers comprising hybrid structures. Such structures, for example peptide-nucleic acids and glycoproteins, are known in the art. The wavelength or wavelengths of the incident light can be chosen to target the absorption maxima of a particular bond, for example the sugar-phosphate bond of a polynucleotide, in order to break the bond at a specific position. In one embodiment, an additional incident wavelength or additional wavelengths can be chosen to ionize each monomeric unit, such as a DNA base, as it emerges from the pore on the vacuum side.

Certain embodiments of the invention provide for a particle source useful for ionizing species, for example, a radioactive source. In some instances the particle source emits a stream of particles from the vacuum side of the pore. In one example, the stream of particles may be incident on the pore or a region near the pore. In one instance, the stream of particles are incident on the vacuum side of the pore. The particle stream may be used to fragment a molecule, in some instances as the molecules emerges from a pore. In some examples, the fragment may be charged, whereas in other examples the fragment may be neutral. In one embodiment, a molecule may be charged after bombardment by the particle stream, but may otherwise be intact. In some embodiments of the invention, bombardment by the particle stream fragments a polymer such that fragments comprising portions of monomeric units are formed. In one instance, a portion of a monomeric unit, at least one monomeric unit, or a portion comprising a plurality of monomeric units are removed from a polymer as they emerge from a pore. The stream of particles emitted by the particle source may be positively charged, negatively charged, or neutral. In some instances, the particle source may emit argon or xenon atoms or cesium(I) ions. In other instances, the particle source may emit electrons.

In some embodiments, a system may comprise an electrospray ionization source that can be used to ionize a molecule. An electrospray ionization source may be operated at any suitable flow rate. For example, a flow rate may be used that is less than about 1000 nL/minute, less than about 500 nL/minute, less than about 100 nL/minute, less than about 25 nL/minute, etc.

In some aspects of the invention, the mass to charge ratio of an ionized species may be determined using mass spectrometry. In certain embodiments, for example, the mass spectrometer utilizes a mass analyzer 11 to separate ions according to the mass to charge ratio. Examples of mass analyzers include sector field, time-of-flight, quadrupole, triple quadrupole, quadrupole ion trap, linear quadrupole ion trap, Fourier transform ion cyclotron, etc. Other techniques will be known to those skilled in the art. In one embodiment, an ionized species may be accelerated within a mass spectrometer by applied electric fields, and the extractor electrode 9 can be perforated so as to allow the transmission of ions within the spectrometer. Magnetic fields may be generated in a region 10 of the mass spectrometer through which the ions travel and induce a deflection in the trajectory of each ion that is related to its charge to mass ratio. At the far end of the mass spectrometer, a single ion detector array 11 registers the location of each ion impingement. The detector array may comprise, for instance, a set of Channeltron (Burle Industries, Inc., Lancaster, Pa.) single ion detectors that are capable of counting ions with high efficiency, in some cases greater than 95% efficiency, and at a high rate, in some instances exceeding 100 million Hertz.

In some embodiments, the mass spectrometers described herein may operate with improved efficiency. For example, as discussed, in some embodiments, the invention allows for mass spectrometry of single molecules with very little signal-to-noise ratio. In some instances, efficiency may be defined as the number of molecules detected by a mass spectrometer divided by the number of molecules entering the mass spectrometer. It should be understood that the efficiency is expressed as a fraction less than or equal to 1 and that the fraction may be multiplied by 100% so as to quantify the efficiency in terms of percentile. For example, the efficiency of the mass spectrometer may be at least about 1%, at least about 5%, at least about 10%, at least about 15%, at least about 25%, at least about 30%, at least about 40%, at least about 50%, at least about 60%, at least about 70%, at least about 80%, at least about 90%, at least about 95%, at least about 98%, or even at least about 99%. In some embodiments, the efficiency of a mass spectrometer may be determined by measuring detector current (caused by the detection of target molecules in the spectrometer) as a function of the incoming flow rate of the target molecules in a sample. The concentration of analyte in a sample may be determined by any number of known methods. For example, the analyte may be quantified by spectroscopic techniques (e.g., UV-vis spectrophotometry, NMR spectroscopy, etc.), enzymatic methods (e.g., coupled enzymatic assays, etc.), HPLC, etc.

In some cases, a reduced size of the pore in the mass spectrometer may allow for increased efficiency of mass spectrometer operation. For example, in some embodiments, reducing the number of ions isolated in a mass spectrometer can improve signal-to-noise ratio of the mass spectrometer. In some instances, a smaller pore diameter may reduce the rate at which molecules pass through the pore, and the pore diameter may even be such that molecules pass through the pore in "single file" fashion. Without wishing to be bound by any theory, a smaller rate at which molecules pass through the pore can lead to a smaller number of ions isolated in the mass spectrometer, which can lead to improved mass spectrometer efficiency. In some embodiments, a mass spectrometer having a pore as described herein may operate with higher efficiency than a mass spectrometer having a pore larger than the pores described herein.

In certain embodiments, the technique can be insensitive to the orientation of a molecule. Additionally, the technique can be insensitive to the rate, or a non-uniform rate, at which molecules or a molecule, such as a biopolymer, translocate the pore. For example, in the case of biopolymer sequencing, the mass of each monomer, or the mass of a fragment that corresponds to a monomer, and the order of detection of the monomers or fragments of monomers are sufficient to determine the sequence of the polymer. In one embodiment, the sequence of masses detected by the mass spectrometer determines the DNA sequence of the candidate molecule. For example, if a DNA molecule containing adenine, cytosine, guanine, and thymine were cleaved at the same chemical bond along the molecule and singly ionized upon entering the mass spectrometer, then four different masses would be detected by the mass spectrometer, each corresponding to a particular DNA base. In this example, the identity of the DNA base may be determined from the mass to charge ratio. Conversely, if the DNA bases or nucleotides are cleaved at different chemical bonds, the identities of the nucleotides or bases can be determined by considering the atomic masses that correspond to the possible DNA base fragments. In this embodiment, the method makes use of the known molecular structure of DNA and the fact that a sequence of nucleotide masses add to form a continuous DNA molecule of a given mass. Alternatively, a tandem mass spectrometer may be employed that utilizes a secondary fragmentation of the initial fragments generated to determine the identity of a species.

Figure 4:
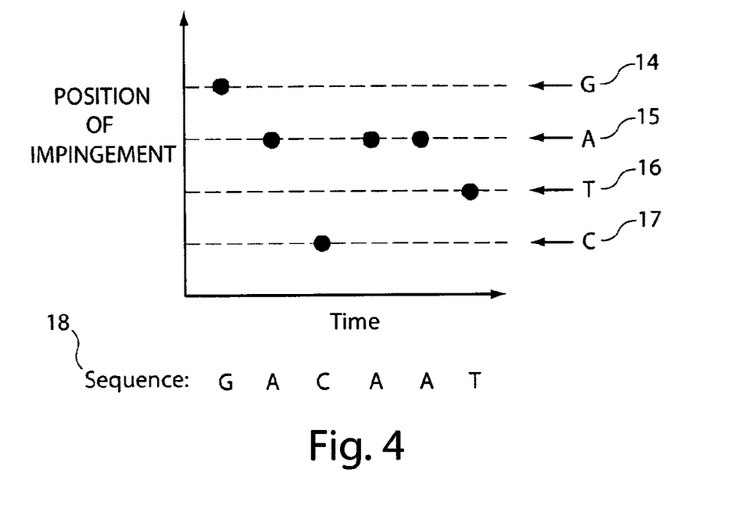
FIG. 4 illustrates the data output from sequencing DNA, in accordance with various embodiments of the invention.

In an embodiment where a DNA molecule is being sequenced using the invention, the sequence of impingement locations can uniquely identify the sequence of the DNA molecule as can be seen in FIG. 4. Because the masses of the four common DNA bases, guanine 14, adenine 15, thymine 16, and cytosine 17, differ from one another, accurate sequence information 18 may be obtained through mass spectrometry. Those skilled in the art will recognize that bases other than adenine, cytosine, guanine, and thymine occur naturally within DNA, for example, methylated derivatives of these bases and damage products of these bases, i.e. from ultraviolet exposure or exposure to oxidants, for example. The disclosed invention also provides for determining these bases as well. A variety of non-naturally occurring bases also exist in the art and may be incorporated into a DNA destined for sequencing. Likewise, naturally occurring and non-naturally occurring alternative amino acids, i.e. those other than the 20 commonly cited naturally-occurring amino acids, may in part make up a polypeptide.

In certain aspects of the invention, detection of various species is provided. In some embodiments, the invention can be used to detect biomarkers within biopolymers. For example, numerous modifications to nucleic acids have been reported to occur in vivo, and many of these modifications have been linked to disease, the risk of disease, or variations in gene expression. For instance, DNA methylation, such as at cytosine residues, can control gene expression in cells. Thus, the present invention may be useful for determining the gene expression profile of a particular cell, i.e. the epigenetic profile of a patient. DNA methylation may also have a role in suppressing tumor suppressor genes, and the determination of DNA methylation within tumor suppressor genes or other regions of the genome may therefore be useful for assaying cancer risk or the specific type of cancer in a patient.

The invention may also be useful in personalized medicine since acquiring genetic information about the cancer cells in a subject may lead to selection of a treatment over another treatment. Other biomarkers may be useful for determining a subject's risk of disease. For instance, the presence of oxidized DNA bases, such as 7,8-dihydro-8-oxoguanine, may be linked to an increased risk of breast cancer and other cancers. Detection of oxidized DNA may also be useful for assaying the risk of other diseases for which oxidative stress is linked, including those diseases associated with chronic inflammation. Examples of such diseases include cardiovascular disease, Alzheimer's disease, aging, Crohn's disease, etc. Biomarkers may also be found in protein, for example nitrotyrosine residues, or in polysaccharides. In other embodiments, the invention may be used to detection of minute quantities of materials. Since the invention allows for mass spectrometry of single molecules with very little signal-to-noise ratio, the invention may be used in diagnostic applications for measuring very small amounts of analytes in bodily materials such as urine, blood, saliva, feces, mucous, etc. In yet another embodiment, the invention can be used for the detection of explosives. In another instance, the invention can be used to detect environmental pollutants or agents.

Polymers that are not biopolymers may also be included as well, in various embodiments. Examples of such polymers include poly(ethylene glycol), poly(lactic acid-co-glycolic acid), polyesters, polyamides, polyurethanes, polyacrylates, polyethylenes, polypropylenes, polyanhydrides, etc. or any other molecule comprised of a plurality of monomeric units. In some cases, the polymer may be a copolymer, for example block copolymers or graft copolymers.

U.S. Provisional Patent Application Ser. No. 61/085,480, filed Aug. 1, 2008, entitled "System and Methods for Determining Molecules using Mass Spectrometry and Related Techniques," by D. M. Stein, is incorporated herein by reference in its entirety.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method, comprising:
    passing a polymer through a non-naturally occurring pore having a diameter of less than about 1 micrometer; and
    cleaving the polymer in sequence to produce one or more fragments.

2. The method of claim 1, wherein the pore has a diameter of less than about 50 nanometers.

3. The method of claim 1, wherein the pore has a diameter of less than about 15 nanometers.

4. The method of claim 1, wherein the pore has a diameter of less than about 5 nanometers.

5. The method of claim 1, wherein the pore has a diameter of less than about 2 nanometers.

6. The method of claim 1, wherein the pore separates a first chamber having a pressure at a first level and a second chamber having a pressure at a second level, the pressure at the first level being less than the pressure at the second level.

7. The method of claim 6, wherein the pressure at a first level is at least 50% less than the pressure at a second level.

8. The method of claim 1, wherein the pore is formed in a solid state material.

9. The method of claim 1, wherein the pore is formed in a polymeric material.

10. The method of claim 1, wherein the pore is formed in a ceramic material.

11. The method of claim 1, wherein the polymer is cleaved using a laser or an electric field.

12. The method of claim 1, wherein cleaved portions of the polymer are determined using mass spectrometry.

13. The method of claim 1, wherein an electric field urges the polymer through the pore.

14. The method of claim 1, wherein a pressure difference urges the polymer through the pore.

15. The method of claim 1, wherein the polymer passes through the pore in single file.

16. The method of claim 1, wherein the pore is defined by a carbon nanotube.

17. The method of claim 1, wherein the polymer is a biopolymer.

18. The method of claim 1, wherein the polymer is a polypeptide or a polysaccharide.

19. The method of claim 1, wherein a fragment is ionized to form a single ion.

20. The method of claim 19, further comprising:
  isolating the single ion in a mass spectrometer;
  generating a signal in the mass spectrometer using the single ion; and
  obtaining a mass spectrograph based on the signal, indicative of the single ion.

21. The method of claim 19, wherein an electric field or a laser is used to generate the single ion.

22. A system, comprising:
  a pore having a diameter of less than about 1 micrometer, separating a low-pressure chamber and a sample chamber;
  a particle source configured to direct particles in the low-pressure chamber towards the pore; and
  a mass detection unit configured to determine ions produced within the low-pressure chamber.

23. The system of claim 22, wherein the pore has a diameter of less than about 50 nanometers.

24. The system of claim 22, wherein the pressure in the sample chamber is lower than the pressure in the low-pressure chamber.

25. The system of claim 22, further comprising a laser directed at the pore.

26. The system of claim 22, further comprising an electric field generator positioned to produce an electric field at the pore.

27. The system of claim 22, wherein the mass detection unit is a mass spectrometer.

28. The system of claim 22, wherein the pore is defined by a carbon nanotube.

* * * * *